(12) United States Patent
Empie et al.

(10) Patent No.: US 7,214,394 B2
(45) Date of Patent: May 8, 2007

(54) POLICOSANOL COMPOSITIONS, EXTRACTION FROM NOVEL SOURCES, AND USES THEREOF

(75) Inventors: Mark W. Empie, Forsyth, IL (US); Ahmad Hilaly, Springfield, IL (US); Alexandra J. Sanborn, Lincoln, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 227 days.

(21) Appl. No.: 10/447,212

(22) Filed: May 29, 2003

(65) Prior Publication Data
US 2004/0034241 A1 Feb. 19, 2004

Related U.S. Application Data

(60) Provisional application No. 60/384,100, filed on May 31, 2002.

(51) Int. Cl.
*A61K 36/00* (2006.01)
(52) U.S. Cl. ............................. 424/757; 424/725
(58) Field of Classification Search ............... None
See application file for complete search history.

(56) References Cited

U.S. PATENT DOCUMENTS

| | | | |
|---|---|---|---|
| 3,031,376 A | 4/1962 | Levin et al. | |
| 4,150,970 A | 4/1979 | Ries et al. | |
| 4,186,211 A | 1/1980 | Debat | |
| 4,420,329 A | 12/1983 | Laughlin | |
| 4,605,430 A | 8/1986 | Godrej et al. | |
| 4,670,471 A | 6/1987 | Clark | |
| 4,714,791 A | 12/1987 | Inada et al. | |
| 4,741,754 A | 5/1988 | Ries | |
| 4,874,794 A | 10/1989 | Katz | |
| 4,981,699 A | 1/1991 | Inada et al. | |
| 5,071,879 A | 12/1991 | Katz | |
| 5,098,896 A | 3/1992 | Muller | |
| 5,106,879 A | 4/1992 | Clark | |
| 5,135,956 A | 8/1992 | Borg et al. | |
| 5,159,124 A | 10/1992 | Bertholet | |
| 5,166,219 A | 11/1992 | Katz | |
| 5,214,071 A | 5/1993 | Muller | |
| 5,296,514 A | 3/1994 | Muller | |
| 5,397,786 A | 3/1995 | Simone | |
| 5,534,554 A | 7/1996 | Katz et al. | |
| 5,663,156 A | 9/1997 | Granja et al. | |
| 5,744,187 A | 4/1998 | Gaynor | |
| 5,856,316 A | 1/1999 | Laguna Granja et al. | |
| 5,948,822 A | 9/1999 | Pope et al. | |
| 5,952,393 A | 9/1999 | Sorkin, Jr. | |
| 6,004,611 A | 12/1999 | Gotoh et al. | |
| 6,197,832 B1 | 3/2001 | Sorkin, Jr. | |
| 6,225,354 B1 * | 5/2001 | Perez | 514/724 |
| 6,235,795 B1 | 5/2001 | Hernandez et al. | |
| 6,261,565 B1 | 7/2001 | Empie et al. | |
| 6,277,430 B1 | 8/2001 | Cain et al. | |
| 6,284,257 B1 | 9/2001 | Khayat et al. | |
| 6,328,998 B1 | 12/2001 | Cavazza | |
| 6,355,274 B1 | 3/2002 | Dartey et al. | |
| 6,465,526 B1 | 10/2002 | Hernandez et al. | |
| 2001/0034338 A1 | 10/2001 | Sorkin, Jr. | |
| 2002/0016314 A1 | 2/2002 | Schersl | |
| 2002/0076432 A1 | 6/2002 | Dartey et al. | |
| 2002/0099099 A1 | 7/2002 | Gamble et al. | |
| 2002/0103139 A1 | 8/2002 | Weisspapir et al. | |
| 2002/0132035 A1 | 9/2002 | Tamarkin et al. | |
| 2002/0183298 A1 | 12/2002 | Schersl et al. | |

FOREIGN PATENT DOCUMENTS

| | | |
|---|---|---|
| EP | 0 654 262 A1 | 5/1995 |
| EP | 1 108 363 A1 | 6/2001 |
| EP | 1 108 364 A2 | 6/2001 |
| EP | 1 108 365 A2 | 6/2001 |
| JP | 62-087537 | 4/1987 |
| JP | 62-089637 | 4/1987 |
| WO | WO 94/07830 | 4/1994 |
| WO | WO 99/48853 | 9/1999 |
| WO | WO 00/78697 A2 | 12/2000 |
| WO | WO 00/78697 A3 | 12/2000 |

OTHER PUBLICATIONS

Willingham et al. (Pesticide Science (1989), vol. 26, No. 2, pp. 123-132).*

CAPLUS English abstract of KR 180453-1999.*

Batista, J., et al ., "Effect of policosanol on hyperlipidemia and coronary heart disease in middle-aged patients. A 14-month pilot study," *Intl. J. Clin. Pharmacol. Ther.* 34:134-137, Dustri-Verlag (1996).

Canetti, M., et al ., "A Two-Year Study on the Efficacy and Tolerability of Policosanol in Patients with Type II Hyperlipoproteinaemia," *Intl. J. Clin. Pharm. Res.* 15:159-165, Bioscience Ediprint Inc. (1995).

Gounj-Berthold, I. and Berthold, H.K. , "Policosanol: Clinical pharmacology and therapeutic significance of a new lipid-lowering agent," *Am. Heart J.* 143:356-365, Mosby, Inc. (Feb. 2002).

(Continued)

*Primary Examiner*—Susan D. Coe
(74) *Attorney, Agent, or Firm*—Kirkpatrick & Lockhart Nicholson Graham LLP (57) ABSTRACT

Compositions, novel isolation sources and processes, and uses for unique policosanol containing compositions are disclosed. Seed and vegetable processing byproduct and/or "waste" streams are disclosed as containing policosanols with various relative amounts of the various long chain fatty/waxy alcohols. The policosanols are isolated and may be combined with other phytochemical/processing products, and are used in numerous food, beverage, health and/or nutraceutical applications.

13 Claims, 2 Drawing Sheets

OTHER PUBLICATIONS

Hamilton, S. and Hamilton, R.J., "Plant Waxes," in *Lipid Chemistry*, Gunstone, F.D., ed., Paul Elek Scientific Books Ltd., London, UK, pp. 199-269 (1972).

Hernández, F., et al., "Effect of Policosanol on Serum Lipids and Lipoproteins in Healthy Volunteers," *Curr. Ther. Res.* 51:568-575, Excerpta Medica (1992).

Joshi, K.C., and Singh, L.B., "Extractives from Heartwoods: Part I. Isolation of Ceryl Alcohol and β-Sitosterol from *Gmelina arborea*," *Z. Naturforsch.* 25b:270-272, Verlag der Zeitschrift für Naturforschung (1970).

Kawanishi, K., et al., "Free Primary Alcohols in Oils and Waxes from Germs, Kernels and Other Components of Nuts, Seeds, Fruits and Cereals," *J. Am. Oil Chem. Soc. (JAOCS)* 68:869-872, American Oil Chemists' Society (1991).

Meguro, S., et al., "Original Communication Solubilization of phytosterols in diacylglycerol versus triacylglycerol improves the serum cholesterol-lowering effect," *Eur. J. Clin. Nut.* 55:513-517, Nature Publishing Group (2001).

Menendez, R., et al., "Policosanol inhibits cholesterol biosynthesis and enhances low density lipoprotein processing in cultured human fibroblasts," *Biol. Res.* 27:199-203, Society of Biology of Chile (1994).

Menéndez, R., et al., "Cholesterol-lowering effect of policosanol on rabbits with hypercholesterolaemia induced by a wheat starch-casein diet," *Brit. J. Nutr.* 77:923-932, CAB International (1997).

Mirkin, A., et al., "Efficacy and Tolerability of Policosanol in Hypercholesterolemic Postmenopausal Women," *Int. J. Clin. Pharm. Res.* 21:31-41, Bioscience Ediprint Inc. (2001).

Piatak, D.M. and Reimann, K.A., "Isolation of 1-Octacosanol From *Euphorbia coroliata*," *Phytochem.* 9:2585-2586, Pergamon Press (1970).

Sirtori, C.R., and Lovati, M.R., "Soy Proteins and Cardiovascular Disease," *Current Atherosclerosis Reports* 3:47-53, Current Science (2001).

Staby, G.L. and De Hertogh, A.A., "β-Sitosterol, Stigmasterol, Campesterol and Octacosanol in Extracts from 'Wedgwood' Iris Shoots," *Hortscience* 7:411-412, American Society for Horticultural Science (1972).

Warth, A.H., ed., "The Natural Waxes," in *The Chemistry and Technology of Waxes 2nd Ed.*, Reinhold Publishing Corporation, New York, NY, pp. 76-341 (1956).

International Search Report for International Patent Application No. PCT/US03/16969, mailed Dec. 22, 2003, European Patent Office, Netherlands.

Patent Abstracts of Japan, English language abstract of JP 62-087537.

Patent Abstracts of Japan, English language abstract of JP 62-089637.

\* cited by examiner

POLICOSANOL COMPOSITIONS, EXTRACTION FROM NOVEL SOURCES, AND USES THEREOF

CROSS-REFERENCE TO RELATED APPLICATIONS

This application claims the benefit of U.S. Provisional Application No. 60/384,100, filed May 31, 2002, the entire contents of which are hereby incorporated by reference.

BACKGROUND OF THE INVENTION

1. Field of the Invention

The present invention relates, in general, to a method of obtaining policosanols from novel sources, and to compositions obtained by such method. The present invention also relate to a method of reducing cholesterol level in humans and animals. The present invention further relates to a composition comprising policosanols, with or without additional additives, in concentrations effective for cholesterol reduction.

2. Related Art

Currently, approximately 20% of the U.S. population has hyperlipidemia or elevated levels of serum cholesterol, which have been implicated as a leading cause of heart disease. More recently, in an effort to understand and alleviate the impact of coronary heart disease (CHD) on the modem world, the lipid profile has been examined more closely. A total cholesterol level is an obvious risk factor; however, a high level of the bulky low-density lipoproteins (LDL) in the blood stream is also cause for concern. These bulky macro proteins can easily get stuck in the intricate cardiovascular system, which leads to further blockage. Furthermore, a low level of the "cleaner" lipoproteins can be harmful as well. High-density lipoproteins (HDL) are compact, heavy macro proteins that move through the system with more precision and actually have beneficial effects as they sweep through arteries and knock loose stuck materials along the way.

Traditional strategies to reduce blood cholesterol levels have typically been to reduce or eliminate dietary intake of cholesterol. However, the normal diet of most western civilized individuals does not comply with these strategies. The health care profession has since put much emphasis on pharmaceutical tools to assist in lowering cholesterol. These statin drugs, or antihypercholesterolemic drugs, such as Lovastatin™, have proven effective; however, there is room for improvement. Statins are effective for only 50% of the people taking them and they cause side effects such as liver disease and muscle weakness.

Plant-derived long chain fatty or waxy alcohols (generically referred to herein as policosanols) have been demonstrated as having biological activity including lipid effects as well as ergogenic effects with benefits in cardiovascular, cerebral and muscular systems. Also, these compounds have activity as growth regulators for plants. 1-Triacontanol, or myricyl alcohol has been demonstrated as being a growth stimulant on a wide range of plants (U.S. Pat. No. 4,150,970). Recently, such compounds have been associated with inhibiting cholesterol biosynthesis and increasing LDL receptor-dependent processing (Menéendez, et al., *Biol. Res.* 27:199 (1994); Brit. J. Nutrition, 77:923 (1997)) with such effects being demonstrated in patients with type II hypercholesterolemia and dyslipidemia associated with non-insulin dependent diabetes mellitus (Mirkin, et al., *Int. J. Clin. Pharm. Res.* 21:31–41 (2001). Other applications that have been reported in the literature include platelet hyperaggregability, ischemia and thrombosis, prevention of drug-induced gastric ulcer and improvement of male sexual activity (WO 94/07830).

Free primary alcohols are found in many plant waxes; e.g., in leaf bark and stem waxes of most plants. Natural plant waxes may be grouped into waxes of palms, grasses and sedges, broad-leaf trees, and narrow-leaf trees (Albin H. Warth in *The Chemistry and Technology of Waxes,* 1956, Reinhold Publishing Corporation, NY. Pp. 76–341). The sugar cane, *Saccharum officinarum* L., of the grass family, order Graminenae, has an appreciable deposit of wax on the surface of the stalks. This wax is of considerable economic value as it is rich in long chain fatty alcohols.

Numerous patents and patent applications describe methods for the isolation and purification of long chain fatty alcohols (see, for example, JP 60-119514; JP 62-87537, U.S. Pat. No. 5,856,316 and WO 94/07830). Waxes from plant sources have been fractionated into different classes such as hydrocarbons, second alcohols, esters, ketones, aldehydes, free alcohols and acids. Usually, long chain free alcohols in plants are present either as free alcohols or as esters of these alcohols with acids. Such esters usually contain an even number of carbon atoms in the range $C_{20}$–$C_{54}$. The long chain free alcohols usually found are straight chain primary alcohols and mainly of an even length ($C_{20}$–$C_{36}$). Sugar cane wax, for example, may contain up to 26% free and esterified long chain alcohols while Carnauba wax may contain up to 52.5% free and esterified long chain alcohols (Hamilton, et al. Plant waxes in *Topics in Lipid Chemistry,* 3:199–269 (1972), F. D. Gunstone (ed.), John Wiley and Sons, Inc., NY).

It is well known in the literature that long chain aliphatic wax alcohols, referred to as policosanols, have anti-cholesterol effects. Gouni-Berthold et al. shows that doses of 10 to 20 mg per day of policosanol lowers total cholesterol (Gouni-Berthold, I. et al., *Am. Heart J,* 143:356–65 (2002)). U.S. Pat. No. 5,952,393 and U.S. Application No. 20010034338A1 disclose a purportedly synergistic anti-cholesterol effect of a composition comprising phytosterols and policosanols. U.S. Pat. No. 6,197,832 discloses the method of administering this composition of phytosterols and policosanols.

European Patent Application EP1 108 365 A2 discloses encapsulated policosanols for use in food applications.

U.S. Pat. No. 3,031,376 discloses the pharmaceutical use of certain long chain fatty alcohols in a method of increasing oxygen utilization.

European Patent Application EP1 108 363 A1 discloses processes for incorporation of long chain alcohols in edible oils.

European Patent Application EP1 108 364 A2 discloses a method for admixture of long chain alcohols in sterol compounds.

U.S. Pat. No. 6,277,403 discloses fat continuous emulsions containing, among other components, long chain alcohols having at least 20 carbon atoms in the alcohol chain.

U.S. Pat. No. 4,981,699 discloses a method for preparing an edible composition by extracting alcohols of 24–34 carbon atoms at subcritical or supercritical conditions and admixing peptides therewith.

U.S. Patent Application No. 2002/0016314A1 discloses compositions for reducing blood cholesterol and triglycerides comprising policosanol esters.

U.S. Pat. Nos. 5,865,316 and 5,663,156, and PCT Publication No. WO94/07830 disclose an extraction method of policosanols out of sugar cane wax and uses of those policosanol mixtures as a treatment for high cholesterol.

U.S. Pat. No. 6,328,998 discloses a method of treating high cholesterol with a pharmaceutically acceptable salt of L-carnitine and hexacosanol.

There are numerous other reports in the art for extraction of long chain alcohols from plant sources. For example, Staby and De Hertogh (*Hortscience* 74:411–412 (1972)) describe a process for separation of octacosanol in extracts from "Wedgwood" iris shots; Joshi and Singh report on the extraction of octosanol from Gmelina arborea (Heartwoods) (Z. Naturforsch, 25:693–694 (1970)); Piatak and Reimann describe isolation of octosanol from Euphorbia Corollata (Phytochemistry, 9:2585–2586 (1970)). Other sources of free primary alcohols in oils and waxes have included germs, kernels and other components of nuts, seeds, fruits and cereals (Kawanishi, et al., JAOCS 68:869–872 (1991)).

Methods in the art have been described for the purification of long chain free alcohols. These include crystallization, chromatographic separation (Hamiton, et al., Plant waxes in *Topics in Lipid Chemistry*, 3:199–269 (1972), F. D. Gunstone (ed.), John Wiley and Sons, Inc., NY), gel permeation chromatography (WO 99/48853); multiple crystallization in different solvents (U.S. Pat. No. 6,225,354; EP 0654262).

Policosanols have been tested directly against statin drugs and they show similar or better total cholesterol reduction while policosanols improved HDL values, as well (Clinical reviews of Dalmer Laboratories).

Addition of policosanols or policosanols combined with other additives to foods will give the consumer who is concerned about lowering their cholesterol easier choices and more palatable options. For example, in 1999, the FDA approved a health claim of soy protein to reduce the risk of coronary heart disease. Studies showed that 25 grams of soy protein (or more) added to a daily diet had a cholesterol lowering effect. However, it has been noted that it is hard for the average consumer to consume 25 grams of soy protein. One object of the present invention would be to add policosanols to food already containing soy protein. The anticholesterol effect of the policosanols combined with the same effects of soy protein would be additive and the consumer would therefore have to consume less soy protein a day to reduce their risk of coronary heart disease. Also, since it is not known specifically how soy protein reduces cholesterol, there is a possibility policosanols and the soy protein would not only have an additive effect, but a synergistic effect as well.

SUMMARY OF THE INVENTION

The present invention provides a method of obtaining policosanols comprising isolating policosanols from novel sources, in particular, from a seed or grain processing stream or a vegetable oil processing stream. The invention also provides a composition obtained by the method of the present invention. The invention further provides a composition comprising policosanols and soy protein isolate, or policosanols and diacylglycerol oil, in concentrations effective for use in food, beverage, or nutraceutical applications for cholesterol reduction. The invention also provides a composition comprising the composition obtained by the method of the present invention and one or more phytochemicals in effective amounts for use in a food, beverage, or nutraceutical application for cholesterol reduction. The invention further provides a method of reducing cholesterol level in humans and animals comprising administering an effective amount of the compositions according to the method of the present invention.

The various objects, advantages, and embodiments of the invention will be clear from the description that follows.

DETAILED DESCRIPTION OF THE INVENTION

Figure 1:
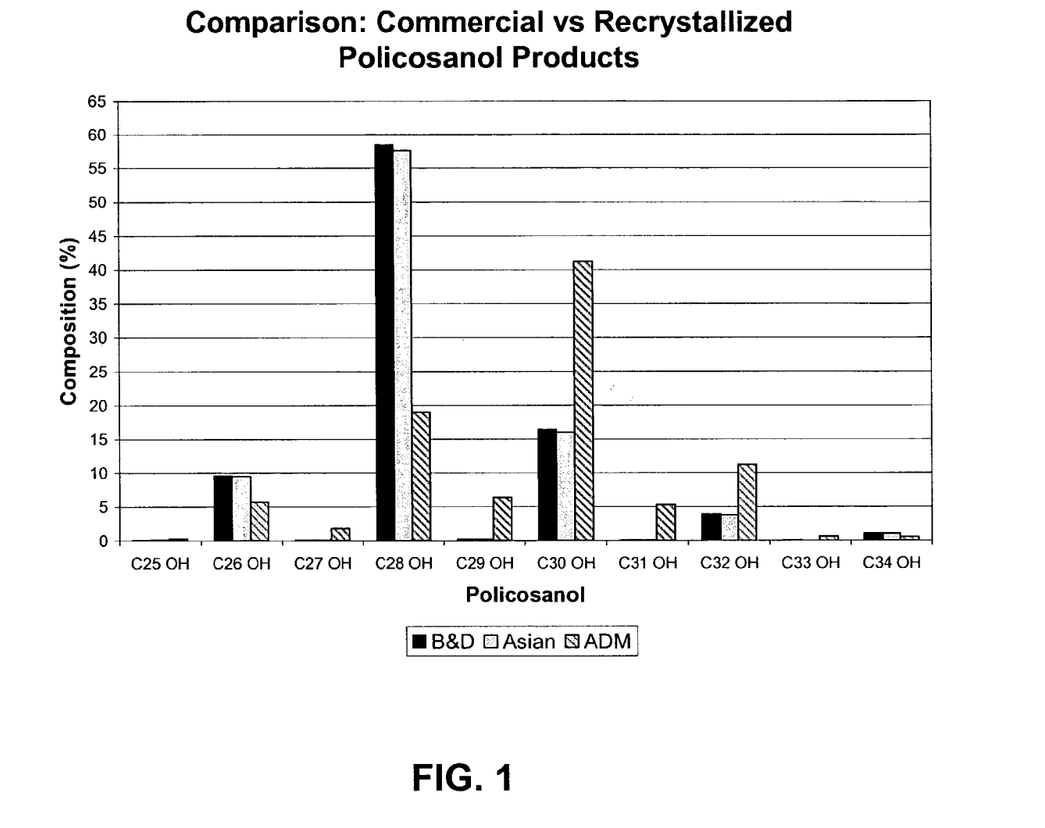
FIG. 1—Comparison of commercially available policosanol products (such as a sample from B&D Nutritional Ingredients Carlsbad Calif. and a sample from Asia) vs. recrystallized policosanol products according to the method of the present invention.
Figure 2:
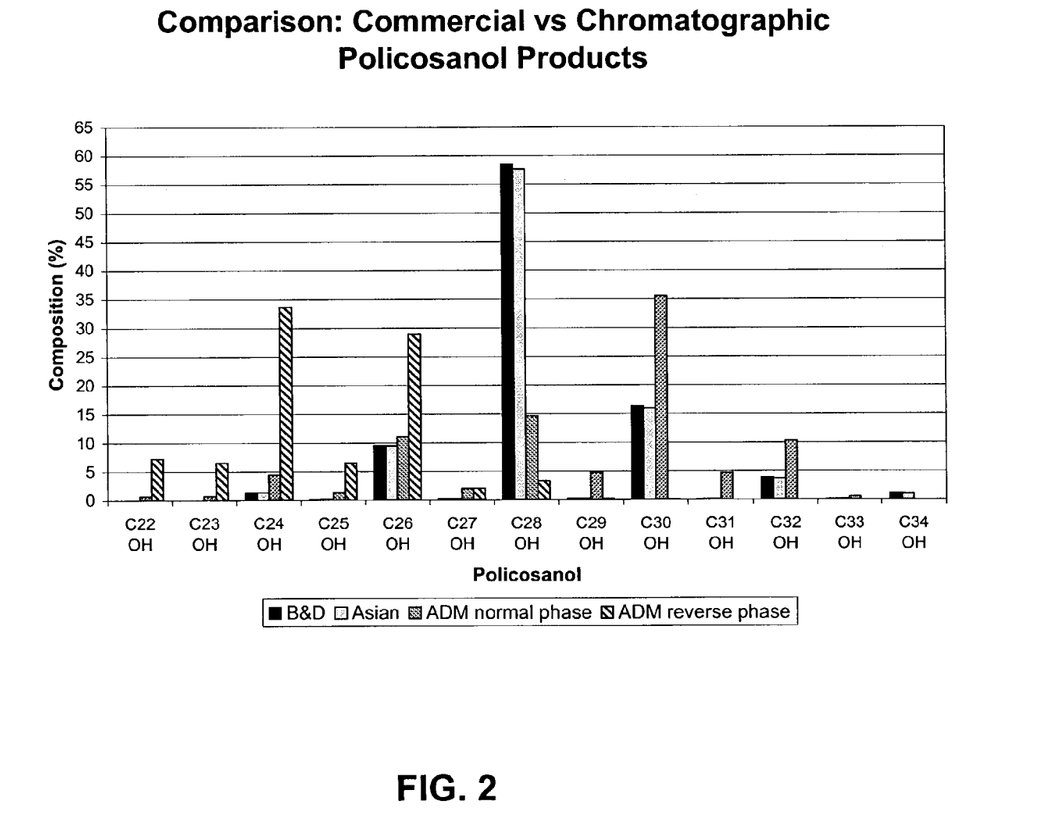
FIG. 2—Comparison of commercially available policosanol products (such as a sample from B&D Nutritional Ingredients Carlsbad Calif. and a sample from Asia) vs. chromatographic policosanol products according to the method of the present invention (obtained using normal phase or reverse phase chromatography)

The present invention relates to compositions for reducing serum cholesterol levels (and depending on the other additives, addressing other health issues), the compositions comprising policosanols having unique long chain fatty alcohol ratios and derived from novel sources, and policosanols combined with other ingredients, useful as additives to foods, to nutraceutical/health products, and the like. Addition of such policosanol comprising compositions into foods and nutraceutical/health would give the consumer a better mode of introduction into the body, and once in the gut, the policosanols are easily broken down. The invention also relates to a method of reducing cholesterol level in humans and animals by administering an effective amount of the compositions of the present invention. For the purpose of this invention, the term policosanols will be defined as long chain, aliphatic wax or fatty alcohols, preferably comprising carbon chain lengths of $C_{20}$–$C_{36}$. The combination of the policosanol compositions of the invention with other active ingredients (such as soy proteins or isoflavones, flax lignans, and other phytochemicals) will provide an opportunity for either additional cholesterol-lowering activity or other various health benefits (reduction of menopausal symptoms, bone health, prostate health, potential anti-cancer effects, etc.). (See, e.g., U.S. Pat. No. 6,261,565B1).

This invention further relates to a method of extracting the policosanols from various sources. It is well known in the art that these policosanols can be extracted from beeswax, rice bran oil, and sugar cane mud; however, it is an object of this invention that policosanols can also be extracted from vegetable material/oilseeds. The method of extracting from such material is to collect the deodorizer distillate and other byproduct/processing streams created during the processing of oilseed for the production of the oils. Such novel sources are subjected to appropriate extraction/separation techniques for isolation and purification of policosanols.

The policosanol compositions of the present invention are unique in that they are derived from novel source materials, and particularly from vegetable oil/oilseed processing streams and/or byproducts. Soy, corn, linseed, sunflower, rice, flax, wheat, and rape seed processing, for example, have been found by the present inventors to give rise to byproduct streams comprising policosanols containing various relative amounts of the long chain fatty alcohols. Policosanols can also be derived from other sources, including oils such as tall oil. Various deodorizer distillates are potential sources. Certain vitamin E processing streams have also been found to contain policosanols, as have filtrates obtained from sterol isolation of deodorizer distillates.

According to a procedure that was developed by the inventors a plant source such as portions of cereals like soybean, linseed, sunflower and wheat may serve as a raw material for extraction of said alcohols. The alcohols may be extracted from the wax portions of these plants, which are recovered usually in their processing. For instance, the waxes from linseed and sunflower are usually extracted with linseed oil and sunflower oil as part of that process. The vegetable oils produced by extraction are usually winterized to improve clarity and appearance of the product. The process of winterization of the vegetable oil involves chilling of the oil to precipitate the waxes followed by filtration with diatomaceous earth to remove them. It has been discovered that such streams of filter aids and other filter media may serve as a source of long chain alcohols. These sources are presently land filled for lack of a better mechanism for disposal. By practicing the embodiments of the present invention those skilled in the art will be able to extract streams rich in long chain alcohols from such sources. Other sources of such compounds may be streams in wheat milling operations that are rich in the wheat germ fraction. Wheat germ is high in oil content and also contains long chain free alcohols. Such streams may serve as a method for providing the raw material for purification of long chain free alcohols.

Particularly useful embodiments of the invention involve the combined use of the policosanols of the invention with soy protein concentrate or isolate. The synergistic combination of policosanols with soy protein is expected to provide a heightened anti-cholesterol effect, whether in foods, beverages, or health supplement/nutraceutical applications. Further additional embodiments combine with policosanols of the invention with such phytochemicals as vitamins, sterols, saponins, phytoestrogens such as lignans and isoflavones, flavinoids, polyphenols, catechins, and the like (see U.S. Pat. No. 6,261,565B1).

For purposes of this disclosure, "food" is used very generically to include any ingested nutrition and/or energy source. For example, baked goods, staples, drinks and beverages, prepared foods such as frozen or non-frozen packaged foods, etc., would all be useful vehicles for the compositions and uses of the present invention. Fat or oil-based foods such as cooking or additive oils, spreads and dressings are also intended to be included. Such products would benefit further if based on diacylglyceride (DAG) oil technology (see, e.g., U.S. Pat. No. 6,004,611). Beyond traditionally defined foods, of course it is clear that the present invention is also useful in the preparation and consumption of nutraceutical products such as health and dietary supplements, along with "health food" products such as breakfast and/or energy bars, shakes and other drinks or beverages, and the like. A policosanol/vitamin E beverage would be particularly beneficial for cholesterol lowering along with vitamin supplementation. Even typically less "healthy" products such as ice creams, and other higher-fat dairy products, as well as chocolates and confections are appropriate for presentation of the present invention to the consumer. Of course, healthy chocolate-based products such as health bars or chews can be used as vehicles for the invention as well.

The policosanols of the present invention are the long chain waxy or fatty alcohols, preferably comprising carbon chain lengths of $C_{20}$ to $C_{36}$. The principal policosanols found in the novel vegetable/oilseed processing stream sources analyzed by the present inventors to date appear to be the $C_{30}$ alcohol, triacontanol, although the $C_{20}$–$C_{36}$ alcohols are also present, and as noted the relative amounts of the specific alcohols appear to vary with source.

The compositions according to the present invention have unique long chain fatty alcohol ratios. In one embodiment, the compositions of the present invention have an octacosanol ($C_{28}$) content of less than about 57%, preferably less than about 50%, more preferably less than about 45%, more preferably less than about 40%, more preferably less than about 35%, more preferably less than about 30%, more preferably less than about 25%, more preferably less than about 20%, more preferably less than about 15%, more preferably less than about 10%, more preferably less than about 5%. In another embodiment, octacosanols are present in the compositions in an amount between 0% and about 57%, preferably between about 2% and about 30%, more preferably between about 2% to about 25%, more preferably between about 2% and about 20%. In a further embodiment, the compositions have a triacontanol ($C_{30}$) content of at least about 17%, preferably at least about 20%, more preferably at least about 25%, more preferably at least about 30%, more preferably at least about 35%, more preferably at least about 40%. In another embodiment, the compositions of the present invention have a tetracosanol ($C_{24}$) content of at least about 3%, preferably at least about 4%, more preferably at least about 5%, more preferably at least about 10%, more preferably at least about 15%, more preferably at least about 20%, more preferably at least about 25%, more preferably at least about 30%, more preferably at least about 33%. In another embodiment, the compositions of the present invention have a hexacosanol ($C_{26}$) content of at least about 10%, preferably at least about 15%, more preferably at least about 20%, more preferably at least about 25%.

In one preferred embodiment, the sources of policosanols are subjected to solid-liquid extractions where the natural alcohols mixture is selectively extracted with adequate organic solvents. Examples of suitable solvents include toluene, heptane, acetone, methanol, ethanol, chloroform, butanone, propanol, ethyl acetate, and others including their mixtures. The extraction is carried out from periods ranging from about 6 to about 24 h. The product is recrystallized using the above mentioned solvents and mixtures thereof and may be subjected to vacuum drying. A pressure of about 25 mm Hg may be used during the vacuum drying stage. The purity of the obtained policosanols mixtures is at least about 50%, preferably at least about 60%, preferably at least about 70%, preferably at least about 80%, preferably at least about 90%, with alcohols ranging from 22 to 34 carbons. The melting point range of attained alcohol mixtures is about 81.7–86.3° C.

In another preferred embodiment, the processing stream is mixed with the solvent of choice and heated to a temperature between about 45° C. to about 70° C., preferably between about 50° C. to about 65° C., more preferably about 60° C. to give a uniform solution and gradually cooled. The mixture is preferably stirred at either about room temperature, about 5° C., or about 0° C.

In a further preferred embodiment, a second stage purification procedures is performed to purify the recrystallized policosanols. The second stage purification can be performed using several different procedures, including solid-liquid extraction, Soxhlet extraction, normal phase chromatography, reverse phase chromatography, and complexation. The specific procedure in the complexation studies entails mixing of the solid extract with calcium bromide in methyl isobutyl ketone (MIBK) at constant heating (at a temperature between about 45° C. to about 70° C., preferably between about 50° C. to about 65° C., more preferably about 60° C.) and stirring for about 1 hour. Following filtration, the solid is washed and placed under vacuum at a temperature between about 45° C. to about 70° C., preferably between about 50° C. to about 65° C., more preferably about 60° C. for about 12 hours. The solid is then stirred in water and filtered to give the product sample. The sample is then washed with a solvent of choice. Washing of the solid extract with either diisopropyl ether or methyl ethyl ketone provides a filtrate of enhance policosanol content.

The proposed procedure for obtaining the higher molecular weight primary aliphatic alcohols has some advantages with regards to those previously reported. One of these advantages is related to its simplicity such that this process is more appropriate for large scale production. Still another advantage of this invention is related to the high degree of purification from a starting source of significantly lower percentage of policosanols relative to those of prior art. Other advantages are related with the degree of purity and the practicality of yield than those reported by the state of the art.

EXAMPLE 1

Various wax streams were obtained from the refining of vegetable oils from the Oil Processing Division of Archer-Daniels-Midland (ADM) Company, Decatur, Ill. These streams were obtained from the filtering step of the vegetable oil refinery where the oils are typically winterized or the deodorization step for purification of the vegetable oils. These processes are well known in the art. The streams analyzed were: Sun/Rape Deodorizer Distillate; Sunflower Deodorizer Distillate; Rape Distillate; Soy Deodorizer Distillate; Rape Seed Deodorizer Distillate; Canola Deodorizer Distillate; and Rice Bran Deodorizer Distillate. Each stream was found to contain at least 4 of the $C_{24}$–$C_{30}$ long chain fatty alcohols.

A portion of the material obtained from various sources was transesterified using Ethanol Potassium Hydroxide to break the ester linkages between long chain alcohols and fatty acids. The streams were: Corn Dewax Cake; Rice Fatty Acid Distillate; Cotton Seed Deodorizer Distillate; Soy Hulls; Sunflower Hulls; Linseed Diatomaceous Earth; Sunflower Oil Dewaxing Cake C; and Sunflower Oil Dewaxing Cake. The composition of the different streams after esterification varied, as expected, but demonstrated the presence of $C_{20}$–$C_{30}$ alcohols in the ester form, suggesting that saponification could be used as an extraction process.

It will be apparent to those skilled in the art that these raw materials may be used as sources for production of a mixture of long chain alcohols. These long chain alcohols may be in free or esterified form and may occur with other phytochemicals such as sterols and tocopherols.

Policosanols, Sterols and Tocopherols

TABLE 1

| Sample Id | Carnauba Wax from Brazil | Refined Beeswax from West Africa | Rice Wax from Punjab INDIA | Crude Candelilla Wax | Crude Beeswax Africa | Crude Beeswax Brazil | Crude Beeswax China | Crude Beeswax Australia |
|---|---|---|---|---|---|---|---|---|
| Total Tocopherols | 0.03 | 2.14 | 0.13 | 3.134 | 1.85 | 0.787 | 0.869 | 0.826 |
| Total Sterols | 0.04 | nd | 0.58 | 0.28 | nd | nd | nd | 0.082 |
| Total Stanols | nd | 0.36 | nd | 0.934 | 0.031 | 0.08 | 0.017 | 0.025 |
| Total Policosanols | 10.66 | 1.18 | 1.06 | 4.106 | 0.244 | 0.34 | 0.261 | 0.4 |
| Delta Tocopherol | 0.03 | 2.10 | 0.13 | nd | nd | nd | nd | nd |
| Beta Tocopherol | nd | nd | nd | nd | nd | nd | nd | nd |
| Gamma Tocopherol | nd | nd | nd | nd | nd | nd | nd | nd |
| Alpha Tocopherol | nd | 0.05 | nd | nd | 0.225 | 0.058 | 0.042 | 0.053 |
| Brassicasterol | nd | nd | nd | nd | nd | nd | nd | nd |
| Campesterol | nd | nd | 0.10 | 0.041 | 0.18 | 0.044 | 0.039 | 0.045 |
| Campestanol | nd | nd | nd | 0.026 | 0.031 | 0.032 | 0.031 | 0.022 |
| Stigmasterol | 0.04 | nd | 0.22 | 0.208 | 0.237 | 0.067 | 0.073 | 0.082 |
| Sitosterol | nd | nd | 0.26 | 0.139 | 0.03 | 0.034 | 0.037 | 0.036 |
| Sitostanol | nd | 0.36 | nd | 1.32 | 0.59 | 0.262 | 0.283 | 0.311 |
| C20 Alcohol | nd | nd | nd | 0.313 | 0.02 | 0.034 | 0.027 | 0.089 |
| C22 Alcohol | nd | 0.02 | nd | 0.824 | 0.458 | 0.225 | 0.292 | 0.166 |
| C23 Alcohol | nd | nd | nd | nd | nd | nd | nd | nd |
| C24 Alcohol | 0.03 | 0.12 | 0.02 | 0.212 | 0.054 | 0.031 | 0.045 | 0.024 |
| C25 Alcohol | nd | nd | nd | nd | nd | nd | nd | nd |
| C26 Alcohol | 0.04 | 0.09 | 0.05 | 0.051 | 0.011 | nd | nd | nd |
| C27 Alcohol | nd | 0.03 | nd | nd | nd | nd | nd | nd |
| C28 Alcohol | 0.49 | 0.14 | 0.08 | ad | nd | nd | nd | nd |
| C29 Alcohol | 0.08 | 0.04 | nd | 0.267 | nd | nd | nd | nd |
| C30 Alcohol | 1.42 | 0.36 | 0.31 | 0.013 | nd | nd | nd | 0.082 |
| C31 Alcohol | 0.07 | 0.03 | nd | 0.061 | nd | nd | 0.008 | nd |
| C32 Alcohol | 6.23 | 0.31 | 0.33 | 0.751 | 0.02 | 0.08 | 0.009 | 0.025 |
| C33 Alcohol | 0.06 | nd | nd | 0.289 | nd | nd | nd | 0.03 |
| C34 Alcohol | 2.20 | 0.04 | 0.21 | 0.123 | nd | nd | nd | nd |
| C35 Alcohol | nd | nd | nd | nd | ad | nd | nd | nd |
| C36 Alcohol | 0.03 | nd | 0.06 | 3.817 | 0.244 | 0.34 | 0.261 | 0.37 |

Results are in g/100 g

TABLE 2

| TRANSESTERIFIED: Results are % w/w | | | | | |
|---|---|---|---|---|---|
| Sample Id | C24 Alcohol | C26 Alcohol | C27 Alcohol | C28 Alcohol | C30 Alcohol |
| Rice Bran DOD 01 | 0.02 | 0.15 | 0.04 | 0.01 | 0.02 |
| Rice Bran DOD 02 | 0.02 | 0.13 | 0.03 | 0.01 | 0.02 |
| Rice Bran DOD 03 | 0.16 | 0.33 | 0.02 | 0.16 | 0.23 |
| Rice Bran DOD 04 | 0.17 | 0.34 | 0.02 | 0.15 | 0.23 |
| Corn Fiber | nd | 0.11 | nd | nd | nd |
| Destarched Corn Fiber | 0.03 | 0.05 | nd | nd | nd |

| Sample Id | C18:1 Alcohol | C18 Alcohol | C20 Alcohol | C22 Alcohol | C24 Alcohol | C26 Alcohol | C27 Alcohol | C28 Alcohol | C30 Alcohol |
|---|---|---|---|---|---|---|---|---|---|
| Corn Dewax Cake--liquid | nd | nd | nd | nd | nd | nd | nd | nd | nd |
| Corn Dewax Cake--solid | nd | nd | nd | nd | 0.02 | 0.01 | nd | nd | 0.01 |
| Rice FAD | nd | nd | nd | nd | 0.01 | 0.02 | nd | 0.01 | 0.02 |
| Cotton Seed DOD | nd | nd | 0.02 | 0.17 | 0.02 | 0.02 | nd | 0.06 | 0.03 |
| Soy Hulls | nd | nd | nd | nd | nd | nd | nd | 0.04 | 0.32 |
| Sunflower Hulls | nd | nd | 0.06 | 0.09 | 0.17 | 0.12 | nd | 0.08 | 0.11 |
| Linseed DE | nd | nd | 0.02 | 0.04 | 0.27 | 0.30 | 0.01 | 0.21 | 0.16 |
| Stearine 6117 | nd | nd | nd | nd | 0.02 | 0.01 | nd | 0.01 | 0.01 |
| Stearine 6126 | nd | nd | nd | 0.02 | 0.10 | 0.08 | nd | 0.06 | 0.03 |
| Stearine 6150 | nd | nd | nd | nd | 0.04 | 0.03 | nd | 0.03 | 0.02 |

| Sample Id | C24 Alcohol | C26 Alcohol | C27 Alcohol | C28 Alcohol | C30 Alcohol |
|---|---|---|---|---|---|
| Sun Oil Dewaxing Cake C | 1.09 | 0.97 | 0.03 | 0.53 | 0.33 |
| Sun Oil Dewaxing Cake F | 1.12 | 0.97 | 0.03 | 0.53 | 0.34 |
| Oelmuhle Leer Rape Distillate | 0.02 | 0.03 | 0.05 | 0.05 | 0.01 |
| Sun/Rape Distillate | 0.02 | 0.28 | 0.04 | 0.17 | 0.01 |
| Sunflower Distillate | 0.03 | 0.48 | nd | 0.04 | 0.03 |
| Canola A | 0.02 | 0.15 | 0.07 | 0.13 | 0.04 |
| Canola B | 0.02 | 0.15 | 0.09 | 0.13 | 0.03 |

EXAMPLE 2

Analytical results obtained to date suggest streams derived during the processing of oilseeds to produce Vitamin E contain various levels of policosanols in various relative amounts of long chain fatty alcohols.

It should also be noted that the ratio of one policosanol to another varies depending on its source. Analysis of one ADM Vitamin E stream shows triacontanol to be the most abundant. In comparison, another ADM Vitamin E stream shows hexacosanol to be the most abundant.

A large portion of this research involved purification via column chromatography. Several sources have been investigated including various DODs and vitamin E streams. The results obtained thus far show the highest level of policosanols to be at least about 90%. In one investigation, policosanols were isolated from the Vitamin E stream using silica gel and a heptane:heptane/acetone elution. In one study, squalene was isolated in at least about 45% and the sterols isolated in at least about 60% purity. Another separation using Vitamin E stream and silica along with a very slow gradient elution of heptane:heptane/acetone provided at least about 62% squalene.

Solid-liquid extraction has also been an area of recent interest. The solvents of choice have been heptane, methanol, water, acetone, isopropanol and mixtures thereof. Quite interestingly, when two streams were subjected to the same extraction conditions (heptane:methanol:water 94:5:1), the policosanols appear in the filtrate in one case and in the solid in the other. Studies performed with a third wax stream showed little or no separation in isopropanol but rather good separation in heptane/methanol/water.

Liquid-liquid extraction is another possible mode of purification. In an effort to better understand the solubility of policosanols, several tests were performed. Recent experiments have shown that policosanols are most soluble in ethers and aromatics.

Another possible starting source for policosanols is in the filtrates obtained from sterol isolation of DODs. Several of the starting DODs showed amounts of policosanols which may have become enhanced with the isolation of sterols.

EXAMPLE 3

Policosanols from rice bran oil were mixed with soy protein isolate or casein in an amount to provide an efficacious does. This material was compounded into a rodent feed and fed to hamsters for a period of 6 weeks. After this time, the animals bled and their serum cholesterol levels were determined.

Materials and Methods

Experimental Animals and Diet

Seventy, 8-week-old male FIB Golden Syrian hamsters (*Mesocricetus auratus*) (BioBreeders, Inc., Watertown, Mass.) approximately nine weeks of age were individually housed in hanging stainless steel wire-bottomed cages at room temperature with a 12-h light:dark cycle and were fed a nonpurified standard diet (Purina Rodent Chow, St. Louis, Mo.) for 1 week to get acclimated to the facility. The hamsters were then fed a semi-purified hypercholesterolemic diet (HCD) (Research Diets, New Brunswick, N.J.) containing 25% casein, 20% hydrogenated coconut oil, 2% corn oil, and 0.12% cholesterol; wt/wt, for a period of 2 weeks. After an overnight fast (12 hr) the hamsters were bled and plasma cholesterol concentrations were measured (week 0). The hamsters were then divided into two groups of ten based on similar mean plasma cholesterol concentrations, and placed on experimental diets for 6 weeks. Group 1 was fed the HCD. Group 2 was fed the HCD plus alcohol extracted waxes. The complete composition of the treatment diets are shown in Table 3. Food disappearance and body weights were monitored on a weekly basis throughout the study, Hamsters were maintained in accordance with the guidelines of the Committee on Animals of the University of Massachusetts Lowell Research Foundation and the guidelines prepared by the Committee on Care in Use of Laboratory Animals Resources, National Research Council (DHEW publication no. 8523, revised 1985).

Plasma Lipoprotein Cholesterol and Triglyceride Measurements

Blood samples were collected after an overnight fast (16 hr) and measured for plasma lipoprotein cholesterol concentrations at weeks 0, 3, and 6. Blood from fasted hamsters, anesthetized with ultrapure 50:50 $CO_2:O_2$ (Northeast Airgas, Salem, N.H.) was collected via the retro-orbital sinus into heparinized tubes and plasma harvested after high-speed centrifugation at 2500×g for 15 min at room temperature. Plasma was frozen at −80° C. until analyzed for plasma total cholesterol (TC), high-density lipoprotein cholesterol (HDL-C), very low- and low-density lipoprotein cholesterol (nonHDL-C), and triacylglycerols (TAG). Plasma cholesterol [21] and triacylglycerols [22] was measured enzymatically and, after the apo B-containing lipoproteins VLDL and LDL were precipitated with phosphotungstate reagent [23], the supernatant was assayed for HDL-C (Sigma, St. Louis, Mo.). Plasma nonHDL-C was calculated from the difference between TC and HDL-C. Accuracy and precisions of plasma lipid and lipoprotein determinations are maintained by participation in the Center for Disease Control—National Heart, Lung, and Blood Institute Standardization Program.

Aortic Cholesterol Measurements

At the end of the exposure period (wk 6), hamsters were anesthetized with an IP injection of sodium pentobarbital and aortic tissue was obtained for determination of cholesterol concentration. The heart and thoracic aorta were removed and stored in phosphate-buffered saline (PBS) at 4° C. for subsequent analysis. To measure cholesterol concentrations in the aortic arch, a piece of aortic tissue extending from as close to the heart as possible to the branch of the left subclavian artery was used (approximately 20 to 40 mg). The tissue was cleaned, weighed, and placed in a vial containing 4 mL of methanol and 10 mL of chloroform. The sample was mixed vigorously and left at room temperature for 48 hr prior to extraction. The solution was then placed in a 37° C. water-bath, under $N_2$. When approximately half of the solution was evaporated, 1 mL of chloroform with 1% Triton-100 was added, mixed, and evaporated to dryness at 37° C. under $N_2$. Two hundred and fifty μL of distilled water was added to the samples, vortexed, and placed in a shaking water-bath at 37° C. for 20 min to solubilize the lipid. After incubation, aortic total and free cholesterol concentrations were determined in triplicate using 25 μL of sample enzymatically (Wako Chemicals, Richmond, Va.) using an ELISA assay. Aortic cholesteryl ester concentration was determined as the difference between the total and the free cholesterol concentrations. A pilot study was conducted to evaluate the extent to which this procedure removed tissue cholesterol. Aortic cholesterol concentrations were determined after tissue was placed in solvent (4 mL of methanol and 10 mL of chloroform) overnight with frequent vigorous mixing and compared with the concentrations obtained following tissue minced or homogenization as reported previously (24). No significant differences in aortic cholesterol content were observed between the different cholesterol extraction procedures.

TABLE 3

Plasma total cholesterol concentrations of hamsters during the 6 week treatment period[1]

mg/dL

| Diet | Wk 0 | Wk 2 | Wk 4 | Wk 6 |
|---|---|---|---|---|
| Casein | 335.7 ± 25.2 | 450.2 ± 34.7[a] | 367.4 ± 35.6[a] | 348.2 ± 18.6[a] |
| Casein & Waxes | 328.8 ± 18.0 | 391.3 ± 50.3[ac] | 320.5 ± 35.3[ab] | 307.1 ± 16.6[b] |

[1]Values are means ± SEM, n = 10. Means in each column with different superscript letters are significantly different at $p < 0.05$.

TABLE 4

Plasma LDL cholesterol concentrations of hamsters during the 6 week treatment period[1]

mg/dL

| Diet | Wk 0 | Wk 2 | Wk 4 | Wk 6 |
|---|---|---|---|---|
| Casein | 238.6 ± 25.3 | 348.5 ± 36.6[a] | 241.8 ± 40.8[a] | 209.4 ± 21.5[a] |
| Casein & Waxes | 228.5 ± 21.2 | 284.1 ± 53.6[ac] | 183.4 ± 40.3[ab] | 169.7 ± 18.8[ab] |

[1]Values are means ± SEM, n = 10. Means in each column with different superscript letters are significantly different at $p < 0.05$.

TABLE 5

Aortic cholesterol concentrations in hamsters following the 6 week treatment perioid[1]

μg/mg of aortic tissue

| Diet | Total Cholesterol | Free Cholesterol | Cholesterol Esters |
|---|---|---|---|
| Casein | 2.83 ± 0.44 | 0.82 ± 0.09 | 2.01 ± 0.45 |
| Casein & Waxes | 2.62 ± 0.44 | 0.96 ± 0.27 | 1.67 ± 0.36 |

[1]Values are means ± SEM, n = 10.

EXAMPLE 4

Policosanols were added to chocolate soy based nutrition beverage with agitation. The product had a pleasing flavor and mouth feel. Five mg. policosanols were incorporated into 180 g. of a standard meal replacement drink by direct addition with vigorous agitation. Policosanols were well suspended, barely visible, and had no perceivable organoleptic impact on the drink. Delivery of the policosanols in this type of application can be improved by drying the two ingredients together, or by spraying the policosanols in a solvent onto the protein product before formulating the drink mix.

EXAMPLE 5

A. Policosanols were added to a clear water nanoemulsion formulation of Vitamin E, ethyl alcohol and a surfactant. The solution formed a paste after the addition. This mixture was then diluted into water in an amount of about 100 mg to 50 ml water and heated. The solution was slightly hazy, but after the policosanols remained suspended for over ten minutes.

B. Policosanols were dissolved into ADM 230 Clear Vitamin E (ingredient containing surfactant, ethanol, and Vitamin E acetate) to deliver the following quantities of policosanol and Vitamin E.

3.82% incorp. rate=5 mg policosanol/30 IU Vitamin E 1.15% incorp. rate =5 mg policosanol/100 IU Vitamin E Both samples were prepared by combining ingredients and placing in a hot water bath (<80° C.) until the solution became transparent. Upon cooling, both solutions became much more viscous and cloudy, with the 3.82% sample becoming wax-like in consistency.

Then attempt was made to deliver equivalent of 5 mg policosanols from the resulting samples above in approximately 100 ml water. Both sample ingredients dissolved in water, creating a slightly opaque, milky solution that was well suspended, with minimal graduation or sediment.

EXAMPLE 6

Policosanols were mixed with a 40% isoflavone concentrate and added to a health bar.

EXAMPLE 7

A. Policosanols were added to a commercial diacylglycerol oil (DAG) in an amount of 5 milligrams per 14 grams of oil. The sample was clear and provides an efficacious dose per serving. Higher concentrations of policosanols in the oil created more turbid and viscores samples.

B. Policosanols were dissolved into DAG oil (using same methods as described for 230 Clear Vitamin E above) at various rates from 0.036% to 8%.

Samples in the 0.036%–0.1% range could be classified as "clear" or non-turbid. Concentrations greater than 0.1% became more turbid and viscous.

EXAMPLE 8

Policosanols were added to an ice cream (soy protein based, but would not be limited to soy). Mouth feel was creamy, with a full fat flavor.

EXAMPLE 9

10 mg policosanols were incorporated into a 57 g healthy nougat-type bar by direct addition. Mechanical incorporation was not difficult, with no perceivable organoleptic impact on the bar.

The ingredients of the healthy nougat-type bar are: Milk chocolate, sucrose, soy isolate, corn syrup, high fructose corn syrup, evaporated milk, alkalized cocoa, natural and artificial flavor, sterol esters, palm kernel oil, diacylglycerol, triacylglycerol and monoacylglycerol oil derived from edible vegetable oils, vitamins and minerals (dicalcium phosphate, magnesium oxide, ascorbic acid, vitamin E acetate, niacinamide, ferrous fumerate, d-calcium pantothenate, zinc oxide, pryidoxine, riboflavin, vitamin A palmitate, thiamin mononitrate, folic acid, biotin, potassium iodide, chromium chloride, sodium molybdate, phytonadione, sodium selenite, cholecalciferol, cyanocobalamin), salt, modified cellulose, soy isoflavone concentrate, natural vitamin E acetate, and policosanols.

EXAMPLE 10

| DAG + policosanols | % by weight | 4000 g batch |
|---|---|---|
| DAG w/poli @ 0.2% | 1.1 | 44 |
| Ultralec P Lecithin | 1 | 40 |
| Water | 97.9 | 3916 |
| Total | 100 | 400 |
| 5.3 mg policosanols/240 g serving | | |

| 230 Clear + policosanols | % by weight | 2500 g batch |
|---|---|---|
| 230 Clear E w/poli @ 1.15% | 0.2 | 5 |
| Water | 99.8 | 2495 |
| Total | 100 | 2500 |
| 5.5 mg policosanols/240 g serving | | |

Processing (both samples):

1. Blend on benchtop mixer for 5 min
2. Homogenize @ 1000 psi single stage homogenization
3. UHT process    90 C. pre-heat
                  140 C. final heat
                  6 second hold
                  65 C. hot fill Note:
Food coloring added to samples to aid in homogenization and thermal processing.

EXAMPLE 11

Policosanol Bar
20 g/bar
Purpose: Produce bar incorporating policosanols at rate of 5 mg policosanols/20 g bar

| Ingredient | grams | % |
|---|---|---|
| ADM Corn Syrup 42/43 | 170 | 37.78% |
| Powdered Milk | 30 | 6.67% |
| Ethyl Vanillin | 4.89 | 1.09% |
| Powdered Sugar | 155 | 34.44% |
| ADM Cocoa D-11-V | 20 | 4.44% |
| Nu Sun Sunflower Oil | 45 | 10.00% |
| Arcon S Soy Protein | 20 | 4.44% |
| Policosanols | 0.11 | 0.02% |
| Water approx | 5 | 1.11% |
| Total | 450 | 100% |

1. Gently heat corn syrup, oil, and ethyl vanillin to pourable consistency.
2. Stir soy protein and powdered milk into corn syrup/ester solution. Mix to uniform consistency.
3. Dry blend sugar, cocoa, policosanols, and masking flavor.
4. Combine ingredients and mix to uniform consistency.
5. Add water in 1 ml increments until desired consistency is achieved.
6. Place in mold and let cool

EXAMPLE 12

A Soxhlet extraction process was performed using 1.5 L of methanol as a solvent for 20 h on 50 g of an ADM vitamin E stream. The obtained extract was left to cool to 25° C., and the solid was collected via Buchner filtration. The solids were then washed with methanol. The methanol extract solids were crystallized using toluene as solvent in a temperature range of 2 to 10° C. and dried in a vacuum oven at 25 inches Hg. The alcohols mixture (0.92 g) which was obtained had a purity amounting to 92.34%. The melting point ranges from 81.3 to 86.9° C. Table 6 shows the qualitative and quantitative composition of the higher molecular weight primary aliphatic alcohols provided by this procedure.

TABLE 6

Qualitative and Quantitative Composition

| Component | % of Each Alcohol |
|---|---|
| Total Policosanols | 92.34 |
| C22 OH | nd[1] |
| C23 OH | nd |
| C24 OH | 0.39 |
| C25 OH | 0.31 |
| C26 OH | 5.68 |
| C27 OH | 1.81 |
| C28 OH | 19.02 |
| C29 OH | 6.40 |
| C30 OH | 41.18 |
| C31 OH | 5.24 |
| C32 OH | 11.18 |
| C33 OH | 0.60 |
| C34 OH | 0.52 |

[1] nd = not detected

EXAMPLE 13

A plant sample of vitamin E stream Cake Fraction from Mixed Tocopherol Dewaxing (33 g) was mixed with toluene (500 mL) and allowed to stir at 20° C. for 20 h. The mixture was subjected to Buchner filtration and rinsed with an additional 50 mL of toluene. The solids were dried in a vacuum oven at 25 inches Hg to provide 4.65 g of policosanols mixture with a purirty of 77.64%. The composition of this mixture is outlined in Table 7.

TABLE 7

Qualitative and Quantitative Composition.

| Component | % of Each Alcohol |
|---|---|
| Total Policosanols | 77.64 |
| C22 OH | 0.81 |
| C23 OH | 0.48 |
| C24 OH | 2.86 |
| C25 OH | 0.92 |
| C26 OH | 9.30 |
| C27 OH | 1.91 |
| C28 OH | 14.58 |
| C29 OH | 4.28 |
| C30 OH | 30.41 |
| C31 OH | 3.69 |
| C32 OH | 7.73 |
| C33 OH | 0.35 |
| C34 OH | 0.32 |

EXAMPLE 14

A plant sample of vitamin E stream Cake Fraction from Mixed Tocopherol Dewaxing (16.7 g) was mixed with a 250 mL solution of 98:2 heptane:acetone (500 mL) and chilled to 5° C. for 18 h. The mixture was subjected to Buchner filtration and rinsed with an additional 30 mL of heptane: acetone. The solids were dried in a vacuum oven at 25 inches Hg to provide a policosanols mixture with a purity of 69.88%. The composition of this mixture is outlined in Table 8.

TABLE 8

Qualitative and Quantitative Composition

| Component | % of Each Alcohol |
|---|---|
| Total Policosanols | 69.88 |
| C22 OH | 6.33 |
| C23 OH | 2.84 |
| C24 OH | 9.82 |
| C25 OH | 1.95 |
| C26 OH | 12.00 |
| C27 OH | 1.76 |
| C28 OH | 10.21 |
| C29 OH | 2.64 |
| C30 OH | 18.00 |
| C31 OH | 2.04 |
| C32 OH | 3.93 |
| C33 OH | 0.18 |
| C34 OH | 0.17 |

EXAMPLE 15

An analytical comparison of the isolated chromatographic samples and the commercially available materials (B&D, Asian) was performed. Table 9 shows the results obtained. Table 10 shows representative results obtained using complexation. An analytical comparison of the recrystallized policosanols according to the method of the present invention and commercially available samples (B&D, Asian) was also performed. Representative results are shown in Table 11.

TABLE 9

Comparison of Commercially Available and Chromatographically Isolated Policosanols Samples.

| Component | Standard B&D | Standard Asian | Policosanol Mix Normal Phase | Policosanol Mix Reversed Phase |
|---|---|---|---|---|
| Total Policosanols | 91.17 | 89.71 | 90.85 | 88.20 |
| C22 OH | nd | nd[1] | 0.66 | 7.24 |
| C23 OH | 0.01 | nd | 0.66 | 6.49 |
| C24 OH | 1.31 | 1.31 | 4.42 | 33.61 |
| C25 OH | 0.11 | 0.12 | 1.34 | 6.47 |
| C26 OH | 9.52 | 9.48 | 11.02 | 28.86 |
| C27 OH | 0.16 | 0.16 | 2.00 | 2.01 |
| C28 OH | 58.42 | 57.60 | 14.66 | 3.28 |
| C29 OH | 0.18 | 0.20 | 4.73 | 0.14 |
| C30 OH | 16.40 | 15.95 | 35.52 | 0.08 |
| C31 OH | 0.08 | 0.08 | 4.66 | nd |
| C32 OH | 3.84 | 3.76 | 10.28 | nd |
| C33 OH | 0.08 | 0.02 | 0.48 | nd |
| C34 OH | 1.06 | 1.03 | nd | nd |
| Total Tocopherols | 0.04 | 0.04 | 0.87 | 0.78 |
| Delta | 0.04 | 0.04 | nd | 0.17 |
| Beta | nd | nd | 0.14 | 0.13 |
| Gamma | nd | nd | 0.46 | 0.40 |
| Alpha | nd | nd | 0.27 | 0.09 |
| Total Sterols | 0.01 | nd | nd | nd |
| Brassicasterol | nd | nd | nd | nd |
| Campesterol | nd | nd | nd | nd |
| Campestanol | nd | nd | nd | nd |
| Stigmasterol | 0.01 | nd | nd | nd |
| Sitosterol | nd | nd | nd | nd |
| Sitostanol | nd | nd | nd | nd |

TABLE 9-continued

Comparison of Commercially Available and Chromatographically Isolated Policosanols Samples.

| Component | Standard B&D | Standard Asian | Policosanol Mix Normal Phase | Policosanol Mix Reversed Phase |
|---|---|---|---|---|
| Stanols | nd | nd | nd | nd |
| Total Hydrocarbons | 0.85 | 0.92 | nd | nd |
| C22 | nd | nd | nd | nd |
| C24 | nd | 0.01 | nd | nd |
| C26 | 0.82 | 0.83 | nd | nd |
| C28 | nd | 0.05 | nd | nd |
| C30 | 0.02 | 0.02 | nd | nd |
| C32 | nd | nd | nd | nd |
| C34 | 0.01 | nd | nd | nd |
| C36 | nd | nd | nd | nd |

[1]nd = not detected.

TABLE 10

Comparison of Complexation Extracts.[1]

| Component | Starting Complex Solid | Washing with Diisopropyl Ether | Washing with Methyl Ethyl Ketone |
|---|---|---|---|
| Total Policosanols | 39.28 | 76.02 | 64.41 |
| C22 OH | 0.62 | 1.44 | 2.49 |
| C23 OH | 0.48 | 1.24 | 1.87 |
| C24 OH | 2.73 | 8.21 | 11.01 |
| C25 OH | 0.79 | 2.46 | 3.00 |
| C26 OH | 6.37 | 18.99 | 19.68 |
| C27 OH | 1.11 | 2.84 | 2.37 |
| C28 OH | 7.23 | 14.90 | 9.96 |
| C29 OH | 1.98 | 3.25 | 1.97 |
| C30 OH | 12.91 | 17.05 | 9.06 |
| C31 OH | 1.53 | 1.80 | 0.98 |
| C32 OH | 3.25 | 3.50 | 1.82 |
| C33 OH | 0.15 | 0.16 | 0.09 |
| C34 OH | 0.14 | nd | 0.08 |
| Total Tocopherols | 0.08 | 0.04 | 5.25 |
| Delta | 0.02 | 0.04 | 1.36 |
| Beta | 0.06 | nd | 0.39 |
| Gamma | nd | nd | 2.68 |
| Alpha | nd | nd | 0.82 |
| Total Sterols | 0.05 | nd | 2.56 |
| Brassicasterol | nd | nd | nd |
| Campesterol | 0.03 | nd | 0.80 |
| Campestanol | nd | nd | nd |
| Stigmasterol | 0.02 | nd | 0.32 |
| Sitosterol | nd | nd | 1.44 |
| Sitostanol | nd | nd | nd |
| Stanols | nd | nd | nd |
| Total Hydrocarbons | 0.10 | 0.92 | 0.29 |
| C22 | nd | nd | nd |
| C24 | nd | 0.01 | nd |
| C26 | nd | 0.83 | nd |
| C28 | 0.03 | 0.05 | 0.13 |
| C30 | 0.07 | 0.02 | 0.16 |
| C32 | nd | nd | nd |
| C34 | nd | nd | nd |
| C36 | nd | nd | nd |

[1]The solid was obtained from complexation of an MTD/heptane extract with CaBr$_2$ in MIBK. This solid was then washed with the listed solvent.

TABLE 11

Comparison of Commercially Available and Recrystallized Policosanol Samples.

| Component | Standard B&D | Standard Asian | Isolated Policosanol Mix | Resubmission of Mix |
|---|---|---|---|---|
| Total Policosanols | 91.17 | 89.71 | 90.24 | 92.34 |
| C22 OH | nd[1] | nd | nd | nd |
| C23 OH | 0.01 | nd | nd | nd |
| C24 OH | 1.31 | 1.31 | 0.39 | 0.39 |
| C25 OH | 0.11 | 0.12 | 0.34 | 0.31 |
| C26 OH | 9.52 | 9.48 | 5.87 | 5.68 |
| C27 OH | 0.16 | 0.16 | 1.76 | 1.81 |
| C28 OH | 58.42 | 57.60 | 18.71 | 19.02 |
| C29 OH | 0.18 | 0.20 | 6.30 | 6.40 |
| C30 OH | 16.40 | 15.95 | 39.92 | 41.18 |
| C31 OH | 0.08 | 0.08 | 5.04 | 5.24 |
| C32 OH | 3.84 | 3.76 | 10.87 | 11.18 |
| C33 OH | 0.08 | 0.02 | 0.54 | 0.60 |
| C34 OH | 1.06 | 1.03 | 0.49 | 0.52 |
| Total Tocopherols | 0.04 | 0.04 | 0.04 | 1.27 |
| Delta | 0.04 | 0.04 | 0.04 | 1.27 |
| Beta | nd | nd | nd | nd |
| Gamma | nd | nd | nd | nd |
| Alpha | nd | nd | nd | nd |
| Total Sterols | 0.01 | nd | 0.31 | 0.08 |
| Brassicasterol | nd | nd | nd | nd |
| Campesterol | nd | nd | nd | nd |
| Campestanol | nd | nd | nd | nd |
| Stigmasterol | 0.01 | nd | 0.12 | nd |
| Sitosterol | nd | nd | 0.19 | 0.08 |
| Sitostanol | nd | nd | 0.20 | 0.15 |
| Stanols | nd | nd | 0.20 | 0.15 |

[1]nd = not detected.

Having now fully described the present invention in some detail by way of illustration and example, for purposes of clarity of understanding, it will be obvious to one of ordinary skill in the art that the same can be practiced by modifying or changing the invention with a wide and equivalent range of conditions, formulations and other parameters thereof, and that such modifications are intended to be encompassed within the scope of the appended claims.

All publications, patents and patent applications mentioned in this specification are indicative of the level of skill in the art to which this invention pertains, and are herein incorporated by reference to the same extent as if each individual publication, patent or patent application was specifically and individually indicated to be incorporated herein by reference.

What is claimed is:

1. A method of obtaining policosanols comprising isolating policosanols from a seed or grain processing stream or a vegetable oil processing stream, wherein the seed or grain processing stream or a vegetable oil processing stream is produced in the processing of soybean.

2. The method of claim 1 wherein said isolating step comprises extracting said policosanols using solid-liquid extraction wherein said policosanols are selectively extracted with an organic solvent, wherein extracted policosanols are obtained.

3. The method of claim 2 wherein said organic solvent is selected from the group consisting of toluene, heptane, acetone, methanol, ethanol, chloroform, butanone, propanol, ethyl acetate, and mixtures thereof.

4. The method of claim 2 wherein said extracting step comprises mixing said processing stream with said organic solvent, followed by heating to about 60° C. and cooling.

5. The method of claim 2 wherein said extracting is carried out for a period from about 6 to about 24 hours.

6. The method of claim 2 wherein said extracting is carried out at a temperature selected from the group consisting of about room temperature, about 5° C and about 0° C.

7. The method of claim 2 further comprising recrystallizing said extracted policosanols using a recrystallization organic solvent, wherein recrystallized policosanols are obtained.

8. The method of claim 7 wherein said recrystallization organic solvent is selected from the group consisting of toluene, heptane, acetone, methanol, ethanol, chloroform, butanone, propanol, ethyl acetate, and mixtures thereof.

9. The method of claim 7 further comprising drying said recrystallized policosanols.

10. The method of claim 9 wherein said drying is performed under vacuum.

11. The method of claim 7 further comprising purifying said recrystallized policosanols.

12. The method of claim 11 wherein said purifying is performed using procedures selected from the group consisting of solid-liquid extraction, Soxhlet extraction, normal phase chromatography, reverse phase chromatography and complexation.

13. The method of claim 1, wherein the seed or grain processing stream or a vegetable oil processing stream produced in the processing of soybean is selected from the group consisting of an oil winterization fraction, a deodorizer distillate, and a deodorizer distillate fraction.

* * * * *